(12) United States Patent
Van Dorpe et al.

(10) Patent No.: US 8,928,867 B2
(45) Date of Patent: Jan. 6, 2015

(54) SPECTROSCOPY USING NANOPORE CAVITIES

(75) Inventors: Pol Van Dorpe, Spalbeek (BE); Chang Chen, Leuven (BE)

(73) Assignees: IMEC, Leuven (BE); Katholieke Universiteit Leuven, Leuven (BE)

( * ) Notice: Subject to any disclaimer, the term of this patent is extended or adjusted under 35 U.S.C. 154(b) by 16 days.

(21) Appl. No.: 13/176,359

(22) Filed: Jul. 5, 2011

(65) Prior Publication Data

US 2012/0170034 A1 Jul. 5, 2012

Related U.S. Application Data

(60) Provisional application No. 61/361,304, filed on Jul. 2, 2010.

(51) Int. Cl.
*G01N 21/00* (2006.01)
*G01N 21/55* (2014.01)
*G01N 21/65* (2006.01)

(52) U.S. Cl.
CPC ............ *G01N 21/658* (2013.01); *G01N 21/554* (2013.01)
USPC .......................................................... 356/72

(58) Field of Classification Search
USPC ............................................ 356/72–73, 301
See application file for complete search history.

(56) References Cited

U.S. PATENT DOCUMENTS

| 2006/0119853 | A1* | 6/2006 | Baumberg et al. | 356/445 |
| 2006/0209413 | A1* | 9/2006 | Kim et al. | 359/577 |
| 2007/0229817 | A1* | 10/2007 | Wang et al. | 356/301 |
| 2011/0036994 | A1* | 2/2011 | Frayling | 250/459.1 |

OTHER PUBLICATIONS

C. Genet et al., "Light in tiny holes", Nature publishing group 05350, vol. 445, Jan. 4, 2007, pp. 39-46.
S. Maier, "Plasmonics: Fundamentals and Applications", Springer, New York, 2007.
M.J. Levene et al., "Zero-Mode Waveguides for Single-Molecule Analysis at High Concentrations", Science, vol. 299, Jan. 31, 2003, pp. 682-686.
C. Chen et al., "Raman scattered photon transmission through a single nanoslit", Applied Physics Letters 96, pp. 061108-1-061108-3, 2010.
M.L. Juan et al., "Self-induced back-action optical trapping of dielectric nanoparticles", Nature physics, vol. 5, Dec. 2009, pp. 915-919.
C. Chen et al., "Focusing Plasmons in Nanoslits for Surface-Enhanced Raman Scattering", Small Journal 2009, 5, No. 24, pp. 2876-2882.
C. Chen et al., "Direct Evidence of High Spatial Localization of Hot Spots in Surface-Enhanced Raman Scattering", Angewandte Chemie Int. Ed. 2009, 48, pp. 9932-9935.

(Continued)

*Primary Examiner* — Abdullahi Nur
(74) *Attorney, Agent, or Firm* — Knobbe Martens Olson & Bear LLP (57) ABSTRACT

A system for assisting in spectrally characterizing or detecting a sample using radiation at a predetermined wavelength or in a predetermined wavelength range is disclosed. In one aspect, the system includes a substrate having a nanopore for excitation of plasmons. The nanopore provides a window through the substrate, wherein a smallest window opening of the window has an average length (L) and an average width (W) both being substantially smaller than 2 µm. The nanopore supports highly confined surface plasmon polaritons and at specific wavelengths resonances are observed, when the conditions for a standing wave are fulfilled. This leads to strong field enhancements and enables single molecule spectroscopy.

19 Claims, 5 Drawing Sheets

(56) References Cited

OTHER PUBLICATIONS

D. Branton et al., "The potential and challenges of nanopore sequencing", Nature biotechnology, vol. 26, No. 10, Oct. 2008, pp. 1146-1153.
P.B. Johnson et al., "Optical Constants of the Noble Metals", Physical Review Letters 11, vol. 6, No. 12, Dec. 15, 1972, pp. 4370-4379.
R. Gordon et al., "Increased cut-off wavelength for a subwavelength hole in a real metal", Optics Express, vol. 13, No. 6, Mar. 21, 2005, pp. 1933-1938.
P. Neutens et al., "Electrical detection of confined gap plasmons in metal-insulator-metal waveguides", Nature photonics, vol. 3, May 2009, pp. 283-286.
J.A. Dionne et al., "Plasmon slot waveguides: Towards chip-scale propagation with subwavelength-scale localization", Physical Review B 73, 2006, pp. 035407-1-035407-9.
R. Zia et al., "Geometrics and materials for subwavelength surface plasmon modes", Optical Society of America, vol. 21, No. 12, Dec. 2004, pp. 2442-2446.
F.J. Garcia-Vidal et al., "Transmission of Light through a single Rectangular Hole", Physical Review Letters 95, Sep. 2, 2005, pp. 103901-1-103901-4.
E.S. Barnard et al., "Spectral properties of plasmonic resonator antennas", Optics Express, vol. 16, No. 21, Oct. 13, 2008, pp. 16529-16537.

* cited by examiner

SPECTROSCOPY USING NANOPORE CAVITIES

CROSS REFERENCE TO RELATED APPLICATIONS

This application claims priority under 35 U.S.C. §119(e) to U.S. provisional patent application 61/361,304 filed on Jul. 2, 2010, which application is hereby incorporated by reference in its entirety.

BACKGROUND OF THE INVENTION

1. Field of the Invention

The disclosed technology relates to the field of sample characterization, and more particularly, to methods and systems for spectroscopy based characterization, such as surface enhancement Raman spectroscopic characterization.

2. Description of the Related Technology

Nano-apertures in metal films attract huge interest in sub-wavelength plasmonics. These nano-apertures find applications in emerging fields such as molecular spectroscopy and nanoparticle optical trapping. The excitation of surface plasmons in such apertures results in large electromagnetic field enhancements, which are useful for applications such as surface enhanced Raman scattering (SERS).

Recently, a gold nanoslit-cavity is developed on a free-standing silicon membrane based on long (several micrometers) slits in a gold film. A strong field enhancement in the nanoslit is demonstrated by Chen et al. and applied for SERS. It could be further improved by equipping it with gratings for SPP excitation or reflection.

The use of individual nano-apertures is furthermore considered as an effective method for single molecule analysis, as analyzing the ionic current that flows through a nanopore can reveal the presence of single molecules in real time. However, although this technology can efficiently be used to show the presence of molecules in a nanopore, it currently lacks the ability to reliably identify the specific molecules.

For single molecule level detection using SERS, it was stated in prior art that a long slit having a length in the range of 2 to 100 µm and a width of around 2 to 5 nm is needed to generate a strongly enhanced optical field. However, to reproducibly and uniformly manufacture slits with such a small width (5 nm range) with a small standard deviation is a big challenge for the standard available state of the art of nanofabrication. Furthermore, for a nanofluidic application, a long nanoslit is difficult to manipulate single analyte molecules as there is an uncertainty of the location and the amount of molecules along the slit.

There is hence a need to improve the geometric design of the nanoslit while at the mean time maintain or further improve the electromagnetic field and transmission resonances.

SUMMARY OF CERTAIN INVENTIVE ASPECTS

Certain inventive aspects relate to efficient methods and systems for performing spectroscopy based characterization measurements (e.g. surface enhanced Raman spectroscopy).

It is an advantage of certain embodiments that surprisingly high signal strengths could be obtained for spectroscopic characterization of samples, using measurements in nanopores. It is an advantage of certain embodiments that the geometric design of the nanopore used allows achieving a surprisingly high electromagnetic field enhancement.

It is an advantage of certain embodiments that methods and systems are provided that are particularly interesting for investigating single molecules.

It is an advantage of certain embodiments that systems and methods are provided that can be used for nanofluidics, e.g. whereby a flow through the nanopore can be provided, enabling analysis of the molecules translocating the pore.

It is an advantage of certain embodiments that the nanopores or nanoslits with a geometry can be substantially more easy to make than long nanoslits known from prior art. It is an advantage of certain embodiments that fabrication of the nanopores, e.g. with a width of about 10 nm, can be precisely be done using semiconductor processing.

It is an advantage of certain embodiments that systems and methods are provided that are tuned for a specific resonance wavelength. It is an advantage of certain embodiments that use can be made of a resonance wavelength shift for obtaining information regarding the sample.

One inventive aspect relates to a system for assisting in optically determining a sample property using radiation at a predetermined wavelength or in a predetermined wavelength range, the system comprising a substrate comprising a nanopore for excitation of plasmons, the nanopore providing a window through the substrate, whereby a smallest window opening of the window has an average length (L) and an average width (W) both being substantially smaller than about 2 µm. The average length (L) and the average width (W) of the smallest window opening may be smaller than twice the smallest free-space wavelength of the predetermined wavelength or the predetermined wavelength range.

The average length of the window opening may be determined as function of the average wavelength of the radiation used for optical characterization and the effective refractive index at the nanopore. The effective refractive index at the nanopore thereby is a function of the width of the nanopore.

The average length (L) and the average width (W) of the nanopore may be selected so that the nanopore acts along its length as a Fabry-Pérot resonator.

The nanopore may be a waveguide resonator supporting a surface Plasmon polariton having a wavelength $\lambda_{SPP}$ function of the average length (L) of the nanopore.

The ratio of the average length (L) to the average width (W) may be smaller than about 100.

The average width (W) of the nanopore may be at least about 5 nm.

The walls of the nanopore may be metallic.

The system furthermore may comprise a detector configured with respect to the nanopore for detecting an optical signal, such as for example a surface enhanced Raman spectroscopy signal or a surface Plasmon resonance signal.

The system furthermore may comprise a radiation source for providing radiation at a predetermined wavelength or in a predetermined wavelength range, configured with respect to the nanopore for excitation of plasmons at the nanopore.

One inventive aspect relates to the use of a system as described above for performing any of a surface enhanced Raman spectroscopy measurement, a surface Plasmon resonance measurement, detecting a presence of a particle in a sample or trapping a particle.

One inventive aspect relates to a method for optically determining a sample property using radiation at a predetermined wavelength or in a predetermined wavelength range, the method comprising providing interaction between a sample and a substrate comprising a nanopore providing a window through the substrate, whereby a smallest window opening of the window has an average length (L) and an average width (W) both being substantially smaller than about 2 µm, irradiating the nanopore so as to excite plasmons at the nanopore, and detecting an optical signal at the nanopore and deriving therefrom a property of the sample.

Providing interaction between a sample and a substrate may comprise providing interaction between a sample and a substrate of a system.

Detecting an optical signal may comprise detecting a surface enhanced Raman spectroscopy response or a surface Plasmon resonance response.

Detecting an optical signal may comprise detecting a shift in an optical resonance frequency of an optical signal at the nanopore and deriving therefrom a presence of an analyte in a sample.

Providing interaction between a sample and a substrate may comprise translocating relatively large molecules, e.g. proteins in the sample, through the window in the substrate.

Certain inventive aspects are set out in the accompanying independent and dependent claims. Features from the dependent claims may be combined with features of the independent claims and with features of other dependent claims as appropriate and not merely as explicitly set out in the claims.

The drawings are only schematic and are non-limiting. In the drawings, the size of some of the elements may be exaggerated and not drawn on scale for illustrative purposes.

Any reference signs in the claims shall not be construed as limiting the scope.

DETAILED DESCRIPTION OF CERTAIN ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in certain embodiments reference is made to a sample property, the latter may be a presence or location of an analyte in the sample or a chemical or physical characteristic of the sample or an analyte thereof.

Where in one embodiment reference is made to a window, reference is made to an opening or pore extending through a substrate, i.e. from a front side to a back side thereof.

Where in one embodiment reference is made to a nanopore, reference is made to a nanosized opening. According to one embodiment each dimension of the nanosized opening may be sufficiently small so that they do not induce the same effect as would be obtained when the dimension would be infinite.

Figure 1:
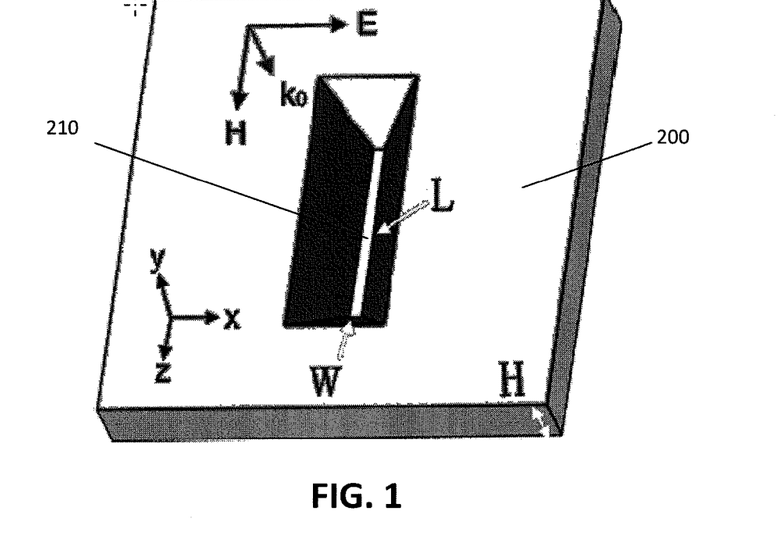
FIG. 1 illustrates a schematic diagram of a single short nanoslit according to one embodiment with a width W and a length L perforated on a gold film of thickness H. The vertex angle of the cavity is 70.5°, made by Si anisotropic etching.

In a first aspect, a system is provided for optically determining a sample property using radiation at a predetermined wavelength or in a predetermined wavelength range or for assisting therein. Such a system may be especially suitable for surface enhanced Raman spectroscopy (SERS), surface plasmon resonance measurements, detection of presence of an analyte in a sample or trapping of a particle in a sample. Optical determination may be spectrometric determination. The system according to one embodiment comprises a nanopore suitable for excitation of plasmons. The nanopore thereby provides a window through the substrate. The window has a smallest window opening of the window has an average length (L) and an average width (W) both being substantially smaller than about 2 µm. Typically, the average length and average width both are smaller than twice the smallest free-space wavelength of the wavelength or wavelength range used for optically determining a sample property. By way of illustration, embodiments of the present invention not being limited thereto, an example of a nanopore that could be used is shown in FIG. 1. FIG. 1 illustrates a substrate 200 having a nanopore 210 providing a window through the substrate 200. The average length (L) and the average width (W) of the smallest window size in the nanopore, also referenced as the average length (L) and the average width (W) of the nanopore, also are indicated in FIG. 1. The nanopore and/or the window created thereby may be substantially rectangular in shape. The average length L and the average width W thereby may be selected so that the nanopore acts along its length as a Fabry-Pérot resonator. Some or all of the walls of the nanopore may be metallic. The nanopore may act as a waveguide resonator supporting a surface Plasmon polariton having a wavelength $\lambda_{SPP}$ function of the average length (L) of the nanopore. The length and width of the Fabry-Pérot may be optimized to enhance the signal intensity at a certain wavelength, e.g. for an excitation wavelength, e.g. for a 785 nm laser to perform Raman experiments. The Fabry-Pérot nanopore cavity according to one embodiment may also be referred to as a "3D nanoslit" because it is having a significant shorter lengths compared to state of the art referred "2D nanoslits" having a long length, which may with respect to the other lengths be considered as an infinite length. The average width W may be large, e.g. more than about 5 nm, e.g. more than about 7 nm, e.g. around 10 nm. This is substantially more wide than state of the art nanoslits used for excitation of plasmons. The use of such a width has several advantages. On the one hand, the nanopores according to one embodiment become suitable for efficiently translocation of relatively large molecules, such as for example relative large biomolecules like proteins. On the other hand, nanopores having a width as described above in combination with a length as described above, are accurately manufacturable using semiconductor manufacturing techniques according to the state of the art. The ratio of the average length (L) to the average width (W) may be smaller than about 100. The ratio of length to width may be adapted so that Fabry-Perot resonance conditions are met. According to one embodiment, the system also may comprise a detector configured with respect to the nanopore for detecting an optical signal, e.g. a surface enhanced Raman spectroscopy signal or a surface Plasmon resonance signal. The system furthermore may comprise a radiation source for providing the radiation at a predetermined wavelength or in a predetermined wavelength range, configured with respect to the nanopore for excitation of plasmons at the nanopore. The system also may comprise an analyzer or analyzing means for analyzing a detected optical signal and deriving therefrom a property of the sample. Such an analyzing means may depend on the particular technique used. Further optional features according to one embodiment and advantages may be as illustrated in the examples. It was surprisingly found that very high enhancement of the field intensity can be obtained. For example, using the rectangular Fabry-Perot (F-P) nanopore-cavity, it is possible to boost the field intensity 100 times higher than the (long) state of the art long nanoslit-cavity devices which can already enhance the field intensity by a factor of around 300 compared to conventional SERS measurements. This means that e.g. to perform Raman Scattering Analysis, the enhancement factor is almost 10000 times higher.

In one aspect, there is the use of a system as described above, for performing any of a surface enhanced Raman spectroscopy measurement, a surface Plasmon resonance measurement, detecting a presence of a particle in a sample or trapping a particle. It thereby is an advantage that use can be made of translocation of particles, even of relative large particles, such as for example proteins.

In another aspect, there is a method for determining a sample property using radiation at a predetermined wavelength or in a predetermined wavelength range. The method may be especially suitable for surface enhanced Raman spectroscopy or scattering, surface Plasmon resonance detection techniques, optical detection of analytes in samples, optical trapping of particles, etc. The method according to one embodiment comprises providing interaction between a sample and a substrate comprising a nanopore providing a window through the substrate, whereby a smallest window opening of the window has an average length (L) and an average width (W) both being substantially smaller than about 2 µm, irradiating the nanopore so as to excite plasmons at the nanopore, and detecting an optical signal at the nanopore and deriving therefrom a property of the sample. In some embodiments detection may be performed of a shift in resonance wavelength, which may be an indication of the presence of a particle or analyte. One embodiment relates to a method wherein detecting an optical signal comprises detecting a shift in an optical resonance frequency of an optical signal at the nanopore and deriving therefrom a presence of an analyte in a sample. More particularly, if the nanopore acts as a Fabry-Pérot resonator, there is a very narrow resonance wavelength, which can be further tuned by the geometrical parameters like length and width. As the Fabry-Pérot resonator is very sensitive to the dielectric constant inside the pore, the presence of analyte molecules can also be detected by checking the slightly shift of the resonance wavelength. In this way one embodiment also provide a new biosensing principle and a new biosensor. The method may advantageously make use of a system as described above.

By way of illustration, embodiments of the present invention not being limited thereby, a number of simulation results are provided illustrating features and advantages of certain embodiments. In order to evaluate the electromagnetic field enhancement factors that can be achieved, simulations were performed for rectangular nanopore cavities with a geometry according to one embodiment. The numerical simulations were 3D finite difference time domain (FDTD) simulations for calculating Maxwell's equations for the complex geometry of a rectangular nanopore-cavity. Here, Lumerical FDTD Solutions software (from Lumerical Solutions, Inc, Canada) was used, allowing visualization of the electromagnetic fields supported by the structures and to study the enhanced electric field intensity $E^2$ inside the nanoslit (pore) and the resonance wavelength $\lambda_{res}$ of sub-wavelength transmission through the nanoslit (pore). To study the plasmonic properties of nanopores with different lengths, a 3D situation (as shown in FIG. 1) was assumed. The nanoslit (pore) was carved in an 800 nm Au film (height H or thickness of the nanoslit), having a fixed width W at the bottom of the pore of 10 nm and various lengths L ranging from 50 nm to 150 nm. To avoid numerical artifacts related to sharp edges, the edges of the nanopore were rounded according to the experimental situation. The tilted angle of the four sides of the cavity was about 55°, corresponding to the angle induced by anisotropic etching of silicon. Although experimentally the Au film is deposited on top of Si, for the case of simplicity, it is assumed that the entire structure is gold. For sufficiently thick Au films, this assumption does not change the conclusions of the simulation. The whole structure was then immersed in water. Perfectly matched layers (PML) were used as the radiation boundary condition. The PML boundaries in light propagation direction were placed 1 μm away from the structure while in other directions were 500 nm away from the structure. The Au layer penetrated through the PML boundaries. A broadband planar source spanning a wavelength range between 600 nm and 1200 nm, was placed above the whole structure. The mesh grid sizes were set to 0.5 nm in the x-axis, 1-2 nm in the y-axis, and 1 nm in the z-axis (as shown in FIG. 1). The permittivity data for Au and water were obtained from literature.

The field intensity spectrum was monitored inside the nanopore, at the maximum enhanced location, while the field (xz) profile was monitored at the middle of the nanopore. The transmission spectrum was obtained by integrating the transmitted light 100 nm below the nanopore. Simultaneously the reflection spectrum was monitored.

For infinitely long nanoslits, it is well known that there is no cut-off for transmission for light polarized perpendicular to the slit (using a similar reference coordinate system as shown in FIG. 1). For a nanopore with all its dimensions well below the free space wavelength, cut-off can be expected. Nevertheless, the gold nanopore supports a highly confined SPP waveguide mode, similar to the mode in a metal-insulator-metal (MIM) plasmon waveguide. This mode has a large effective index, enabling resonance conditions even for very small sizes. Generally, the resonance condition depends on the width and the length of the nanopore and the dielectric constant inside the nanopore. The nanopore-cavity was studied in water, as this kind of devices is typically used in aqueous environment for molecular detection or manipulation. The presence of water already shifts the resonance to longer wavelengths compared to air. In 2D simulations on nanoslit-cavities in air, the resonance is very broad. The enhancement mainly depends on the width of the nanoslit. A smaller gap has stronger electrostatic interaction (SPP coupling) and exhibits a stronger field enhancement. In water, as shown in FIG. 2, the field intensity for the long nanoslit (2D) was similar with the work done by Chen et al before.

Figure 2A:
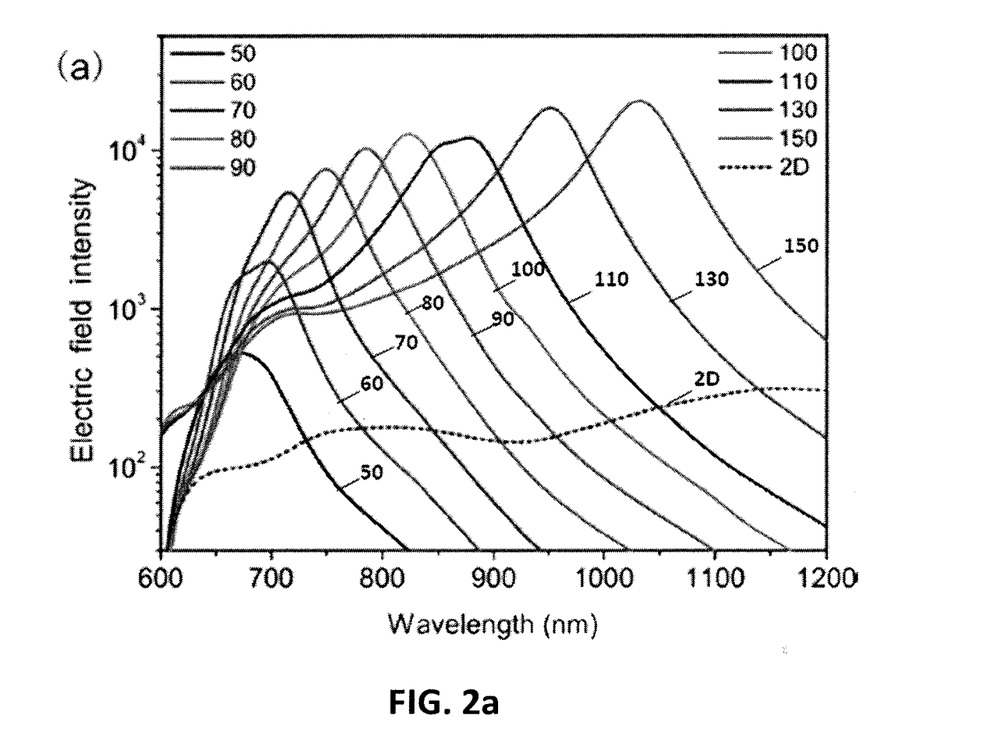
FIG. 2A illustrates Electric field intensity E2 spectra of the nanoslit according to one embodiment with a fixed width of 10 nm but with various lengths.
Figure 2B:
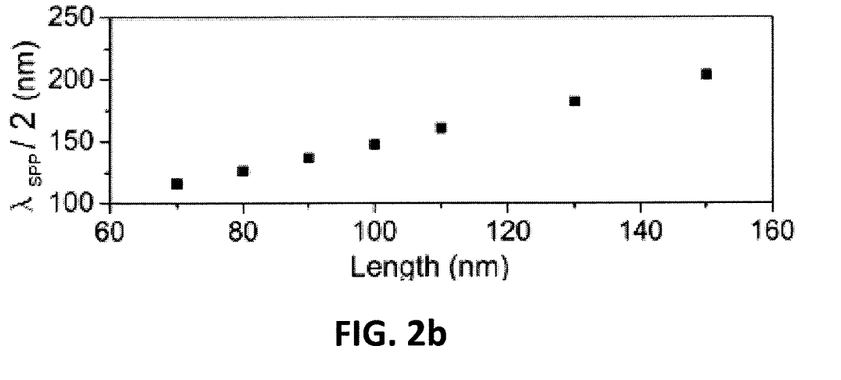
FIG. 2B illustrates a plot of $\lambda_{SPP}/2$ at the resonance wavelengths determined in FIG. 2A versus the corresponding length of the rectangular nanoslit (pore) according to one embodiment.
Figure 3:
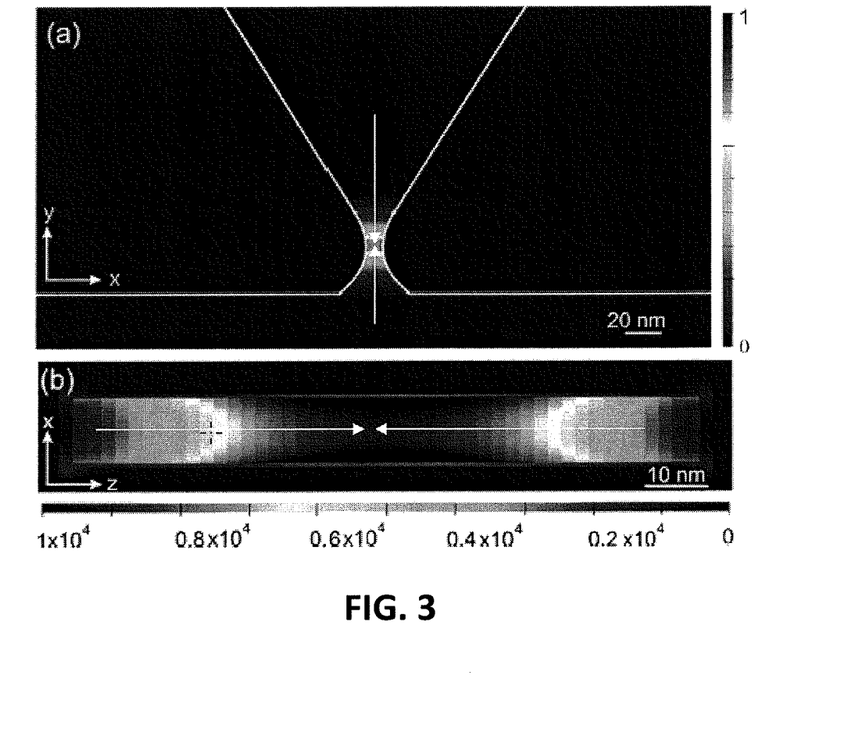
FIG. 3 illustrates (a) the calculated SPP mode in the nanoslit (pore) according to one embodiment for a free-space wavelength of 785 nm and (b) the Electric field intensity E2 top view profile (xz-view) inside the nanoslit (pore) (W=10 nm, L=90 nm) under illumination at 785 nm according to one embodiment.

FIG. 2(a) shows the numerically evaluated maximum field enhancement inside the nanopore for different lengths and the field enhancement in the nanoslit (2D, corresponding with an infinitely long nanoslit). The lengths tested for the nanopores varied from 50 to 150 nm. The reflection and transmission spectra (not shown here) exhibit a similar behavior of resonance wavelengths. Clear and strong resonances were observed, with a field intensity enhancement exceeding the 2D situation with two orders of magnitude. Moreover, the resonance position strongly depends on the length of the pore, consistent with a Fabry-Pérot resonance picture. In order to investigate this hypothesis, the integrated mode solver of Lumerical FDTD was used to calculate the 2D nanopore SPP mode (xy) profile. An example SPP mode profile at 785 nm, shown in FIG. 3(a), is highly localized near the edges of the nanopore. The white arrows give the direction of increasing signal intensity This is reflected as well in the very high mode index, which is near 3 for most of the investigated free space wavelengths. Based on the effective index of the SPP mode, we can calculate the resonance condition of the rectangular nanopore. For a first order odd Fabry-Pérot resonance mode, it is expected that $2L_{res}(2\pi/\lambda_{SPP})+2\phi=2\pi$, with $L_{res}$ the length of the slit at the resonance wavelength, $\lambda_{SPP}$ the wavelength of SPP mode inside the nanopore and $\phi$ the phase pick-up upon reflections at the end of the nanopore. For $\phi=0$, the resonance condition is fulfilled when $L_{res}/\lambda_{SPP}/2$. Therefore, as the phase pick up is not known, for the different lengths and their corresponding free-space resonance wavelengths in the transmission spectra, $\lambda_{SPP}/2$ is calculated and plotted versus the real length in FIG. 2(b). There is a clear linear relation between $L_{res}$ and $\lambda_{SPP}/2$. From the slope of the curve, we can deduce the phase pick-up at the edges of the rectangular nanopore, and estimate it to be about $\pi/2$, in good agreement with other plasmonic resonators. Detailed investigations of the field profile along the nanopore (as shown in FIG. 3(b)) indeed indicate a $\lambda_{SPP}/2$ resonance, with the field going to zero near the ends of the nanoslit. This is expected since the cavity is truncated by metal. In FIG. 3(b) the white arrows indicate the direction of increasing signal strength.

The above described results and simulations illustrate that he Fabry-Pérot resonance obtained by the nanoslit according to one embodiment can result in both a clearly narrowed resonance condition and a strongly enhanced field at the resonance wavelength compared to the 2D situation. In the long (state of the art) nanoslits, the enhancement was optimized by either reducing the size of the gap or adding reflective gratings next to the slit. However, fabricating nanoslits with dimensions reproducibly below 10 nm is still challenging. Using the much shorter nanoslit according to one embodiment makes it possible to obtain resonance conditions which strongly enhance the energy in the nanoslit (nanopore) and correspondingly create a strong field enhancement. Controlling the length of the nanoslit in combination with the width of the nanoslit and the thickness of the substrate in which the slit is made according to one embodiment allows tuning the resonance to the correct wavelength. For instance, a 785 nm laser is commonly used in SERS. Simultaneously one can take advantage of the clearly defined and narrow resonance for local surface plasmon resonance purposes or plasmonic force trapping within the rectangular nanoslit of one embodiment.

Numerical calculations (as explained above) illustrate that the plasmonic properties of the rectangular nanoslits according to one embodiment can be significantly enhanced with varying lengths. It is observed that Fabry-Pérot resonances of highly confined SPP modes in the nanoslits are leading to strong field enhancements in the nanoslit (gap) and are greatly exceeding the case of the infinitely long state of the art nanoslits. An enhancement factor of the field intensity of $10^4$ is obtained even in a 10 nm nanoslit (pore) at $\lambda_{res}$. Due to the narrow bandwidth of the resonance near $\lambda_{res}$, the device of one embodiment shows a high selectivity to the incident beams. Simultaneously, the $\lambda_{res}$ of the nanoslit (pore) pore can also be tuned easily by simply changing the length of the nanoslit.

Figure 4:
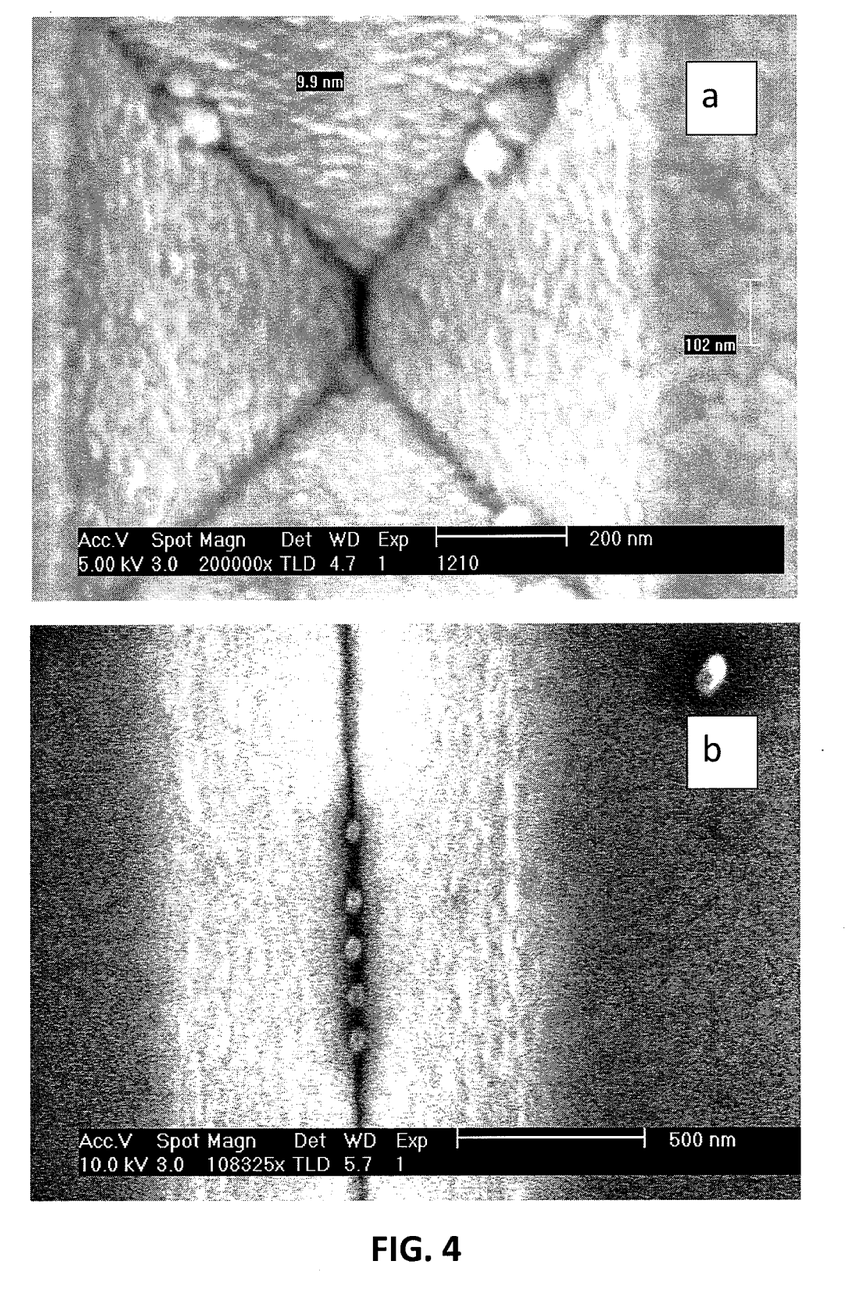
FIG. 4 illustrates scanning electron miscroscopy images of a Fabry-Pérot nanopore (10 nm×100 nm) without any Raman analyte (FIG. 4 picture a) and of a long nanoslit (10 nm×6000 nm) with five carbonaceous beads as the Raman analyte (FIG. 4 picture b), comparing one embodiment with a long nanoslit.

Further by way of illustration, embodiments of the present invention not being limited thereto, experimental results illustrating features and advantages are further discussed. The experimental results illustrate SERS results obtained for a Fabry-Pérot nanopore according to one embodiment compared with a long nanoslit, indicating surprisingly high efficiency for the Fabry-Pérot nanopore. FIG. 4 illustrates scanning electron microscopy images of the Fabry-Pérot nanopore according to one embodiment (FIG. 4, picture a) and of a long nanoslit (FIG. 4, picture b). The Fabry-Pérot nanopore has a size of 10 nm×100 nm and has been shown without any Raman analyte being present. The long nanoslit has a size of 10 nm×6000 nm and has been shown with five carbonaceous beads present as the Raman analyte.

Figure 5:
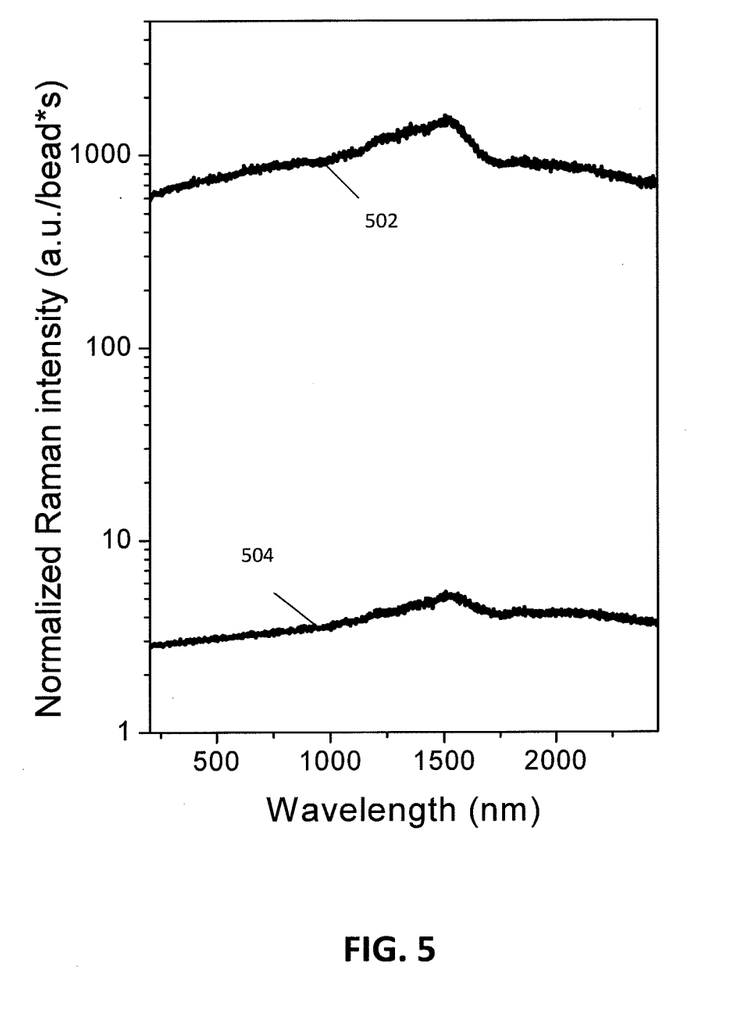
FIG. 5 illustrates SERS spectra for a Fabry-Pérot nanopore according to one embodiment and a long nanoslit.

In FIG. 5, the SERS spectra are shown for the Fabry-Pérot nanopore (spectrum 502) and for the long nanoslit (spectrum 504). The SERS spectra are recorded using an excitation laser having a wavelength of 633 nm and an intensity of about 0.1 W/μm². The intensity of the Raman spectra are normalized by the integration time and the amount of bead, for allowing appropriate comparison between the nanopore and nanoslit results. Carbonaceous nanoparticles are used as Raman analytes, whereby for the nanopore one bead is used and for the nanoslit five beads are used. The size of the beads is about 20 nm and the beads are deposited by electron beam induced deposition. The integration time used for measuring of the SERS spectra is 10 s and 2 s for the nanoslit and the nanopore respectively.

The normalized spectra indicate a surprisingly high intensity difference for the nanoslit and for the nanopore. It can be seen that the SERS intensity is more than a factor 100 higher when using a nanopore compared to the situation using a nanoslit, resulting in the nanopores being especially advantageous for SERS.

Figure 6:
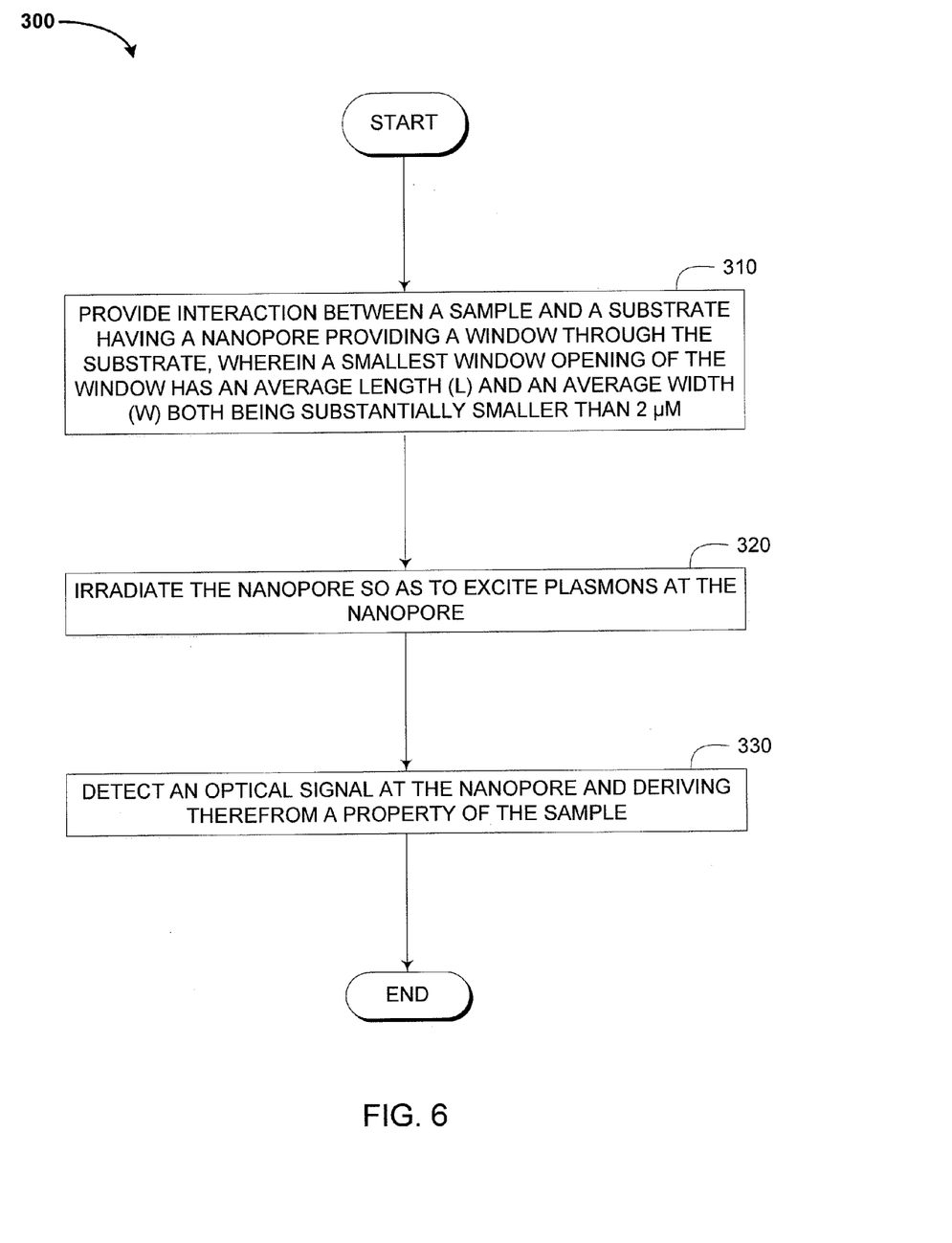
FIG. 6 shows a flowchart of one embodiment of a method of optically determining a sample property using radiation at a predetermined wavelength or in a predetermined wavelength range.

FIG. 6 shows a flowchart of one embodiment of a method of optically determining a sample property using radiation at a predetermined wavelength or in a predetermined wavelength range. The method 300 includes, at a block 310, providing interaction between a sample and a substrate comprising a nanopore providing a window through the substrate, wherein a smallest window opening of the window has an average length (L) and an average width (W) both being substantially smaller than about 2 μm. The method may further include, at a block 320, irradiating the nanopore so as to excite plasmons at the nanopore. The method may further include, at a block 330, detecting an optical signal at the nanopore and deriving therefrom a property of the sample.

The foregoing description details certain embodiments of the invention. It will be appreciated, however, that no matter how detailed the foregoing appears in text, the invention may be practiced in many ways. It should be noted that the use of particular terminology when describing certain features or aspects of the invention should not be taken to imply that the terminology is being re-defined herein to be restricted to including any specific characteristics of the features or aspects of the invention with which that terminology is associated.

While the above detailed description has shown, described, and pointed out novel features of the invention as applied to various embodiments, it will be understood that various omissions, substitutions, and changes in the form and details of the device or process illustrated may be made by those skilled in the technology without departing from the spirit of the invention. The scope of the invention is indicated by the appended claims rather than by the foregoing description. All changes which come within the meaning and range of equivalency of the claims are to be embraced within their scope.

What is claimed is:

1. A system for assisting in optically determining a sample property of a sample using radiation at a predetermined wavelength or in a predetermined wavelength range, the system comprising:
   a substrate;
   and a rectangular nanopore for excitation of plasmons, the nanopore providing a window comprising an opening extending through the substrate thereby allowing a flow through the nanopore enabling analysis of the sample translocating through the nanopore, wherein a smallest window opening of the window has an average length (L) and an average width (W) both being substantially smaller than 2 μm, wherein the average length (L) and the average width (W) of the nanopore are selected so that the nanopore acts along its length as a Fabry-Pérot resonator.

2. The system according to claim 1, wherein the average length of the window opening is determined as function of the average wavelength of the radiation used and the effective refractive index at the nanopore.

3. The system according to claim 1, wherein the nanopore is a waveguide resonator supporting a surface Plasmon polariton having a wavelength $\lambda_{SPP}$ function of the average length (L) of the nanopore.

4. The system according to claim 1, wherein the ratio of the average length (L) to the average width (W) is smaller than about 100.

5. The system according to claim 1, wherein the average width (W) of the nanopore is at least about 5 nm or wherein the average length (L) is in a range from 50 nm to 150 nm.

6. The system according to claim 1, wherein the walls of the nanopore are metallic.

7. The system according to claim 1, the system further comprising a detector configured to detect an optical signal at the nanopore.

8. The system according to claim 1, the system further comprising a radiation source configured to provide radiation at a predetermined wavelength or in a predetermined wavelength range and to excite plasmons at the nanopore.

9. Use of a system according to claim 1 for performing any of a surface enhanced Raman spectroscopy measurement, a surface Plasmon resonance measurement, detecting a presence of a particle in a sample or trapping a particle.

10. The system according to claim 1, wherein the opening extending through the substrate comprises a through hole in the substrate that extends from an opening in a front side of the substrate to an opening in a back side of the substrate.

11. A method of optically determining a sample property using radiation at a predetermined wavelength or in a predetermined wavelength range, the method comprising:
   providing interaction between a sample and a substrate comprising a rectangular nanopore providing a window comprising an opening extending through the substrate thereby allowing a flow through the nanopore enabling analysis of the sample translocating through the nanopore, wherein a smallest window opening of the window has an average length (L) and an average width (W) both being substantially smaller than 2 μm, wherein the average length (L) and the average width (W) of the nanopore are selected so that the nanopore acts along its length as a Fabry-Pérot resonator;

irradiating the nanopore so as to excite plasmons at the nanopore; and detecting an optical signal at the nanopore and deriving therefrom a property of the sample.

12. The method according to claim 11, wherein the process of detecting an optical signal comprises detecting a surface enhanced Raman spectroscopy response or a surface Plasmon resonance response.

13. The method according to claim 11, wherein the process of detecting an optical signal comprises detecting a shift in an optical resonance frequency of an optical signal at the nanopore and deriving therefrom a presence of an analyte in a sample.

14. The method according to claim 11, wherein the process of providing interaction between a sample and a substrate comprises translocating proteins in the sample through the window in the substrate.

15. The method according to claim 11, wherein the nanopore is a waveguide resonator supporting a surface Plasmon polariton having a wavelength $\lambda_{SPP}$ function of the average length (L) of the nanopore.

16. The method according to claim 11, wherein the ratio of the average length (L) to the average width (W) is smaller than about 100.

17. A system for optically determining a sample property using radiation at a predetermined wavelength or in a predetermined wavelength range, the system comprising:

means for providing interaction between a sample and a substrate comprising a rectangular nanopore providing a window comprising an opening extending through the substrate thereby allowing a flow through the nanopore enabling analysis of the sample translocating through the nanopore, wherein a smallest window opening of the window has an average length (L) and an average width (W) both being substantially smaller than 2 μm, wherein the average length (L) and the average width (W) of the nanopore are selected so that the nanopore acts along its length as a Fabry-Pérot resonator;

means for irradiating the nanopore so as to excite plasmons at the nanopore; and means for detecting an optical signal at the nanopore and deriving therefrom a property of the sample.

18. The system according to claim 17, wherein the detecting means comprises means for detecting a surface enhanced Raman spectroscopy response or a surface Plasmon resonance response.

19. The system according to claim 18, wherein the detecting means comprises means for detecting a shift in an optical resonance frequency of an optical signal at the nanopore and deriving therefrom a presence of an analyte in a sample.

* * * * *

UNITED STATES PATENT AND TRADEMARK OFFICE
CERTIFICATE OF CORRECTION

| | | |
|---|---|---|
| PATENT NO. | : 8,928,867 B2 | Page 1 of 1 |
| APPLICATION NO. | : 13/176359 | |
| DATED | : January 6, 2015 | |
| INVENTOR(S) | : Van Dorpe et al. | |

It is certified that error appears in the above-identified patent and that said Letters Patent is hereby corrected as shown below:

In the Claims

In column 12 at line 23, In Claim 19, change "18" to --17--.

Signed and Sealed this
Eighth Day of September, 2015

Michelle K. Lee
*Director of the United States Patent and Trademark Office*